United States Patent [19]

Takayama

[11] Patent Number: 4,799,482

[45] Date of Patent: Jan. 24, 1989

[54] STONE DISINTEGRATOR APPARATUS

[75] Inventor: Syuichi Takayama, Tokyo, Japan

[73] Assignee: Olympus Optical Co., Ltd., Tokyo, Japan

[21] Appl. No.: 916,714

[22] Filed: Oct. 8, 1986

[30] Foreign Application Priority Data

Oct. 18, 1985 [JP] Japan .............................. 60-233089
Oct. 18, 1985 [JP] Japan .............................. 60-233090

[51] Int. Cl.[4] .............................. A61B 17/22
[52] U.S. Cl. .............................. 128/328
[58] Field of Search .............................. 128/328, 24 A, 422; 367/147

[56] References Cited

U.S. PATENT DOCUMENTS 3,230,506 1/1966 Hellund .............................. 367/147
3,234,429 2/1966 Schrom .
3,483,514 12/1969 Barbier et al. .............................. 367/147
3,735,764 5/1973 Balev et al. .............................. 128/328
4,191,189 3/1980 Barkan .............................. 128/328
4,463,825 8/1984 Lerwill .............................. 367/147
4,595,019 6/1986 Shene et al. .............................. 128/328

FOREIGN PATENT DOCUMENTS 0082508 6/1983 European Pat. Off. .............................. 128/328
2635635 2/1978 Fed. Rep. of Germany .............................. 128/328

*Primary Examiner*—Ruth S. Smith
*Attorney, Agent, or Firm*—Frishauf, Holtz, Goodman & Woodward

[57] ABSTRACT

A stone disintegrator apparatus includes a main capacitor for receiving power from a power source, a charge circuit for charging the main capacitor, and a discharge circuit which is turned on during the discharge so as to supply a charge of the main capacitor to discharge electrodes. There is also provided a switch member, e.g., a discharge lamp to be de-energized during the discharge, for electrically isolating the main capacitor from the power source so as to disintegrate a stone in an internal organ.

15 Claims, 10 Drawing Sheets

STONE DISINTEGRATOR APPARATUS

BACKGROUND OF THE INVENTION

The present invention relates to a stone disintegrator apparatus for disintegrating a stone formed in an internal organ.

A typical conventional stone disintegrator apparatus comprises a charge circuit for charging a capacitor connected to discharge electrodes and a discharge circuit for discharging the capacitor to disintegrate the stone. In this stone disintegrator apparatus, charging must be stopped while the capacitor is discharged. For this reason, a switch is connected to one of the power source lines. Alternatively, a relay switch with a contact is arranged so as to switch between the charge and discharge circuits.

In such a conventional stone disintegrator apparatus, since one of the power source lines is opened during the discharge, the discharge current from the charged capacitor is supplied through the other power source line, thus increasing current consumption and endangering a patient. If the relay switch is used, a large current is supplied through the relay contact during the discharge, thus posing a problem of durability of the relay contact. It is desired that a stone in an internal organ is disintegrated at a high speed and in an efficient manner in order to reduce physical pains and danger to the patient. If charging/discharging is switched by the relay, a switching speed exceeding a predetermined value cannot be obtained because of the inertia of the drive portion of the relay. For this reason, the stone disintegration charge and discharge frequencies are limited. In order to solve this problem, a high-speed relay may be used. However, use of the high-speed relay leads to high costs.

SUMMARY OF THE INVENTION

It is an object of the present invention to provide a stone disintegrator apparatus capable of preventing current leakage.

According to the stone disintegrator apparatus of the present invention, a member for isolating a capacitor discharge circuit from a power source during the discharge is provided. This isolating member comprises a relay.

During the discharge, a discharge lamp or a relay switch arranged between the discharge circuit and the power source circuit is opened to completely isolate the discharge circuit from the power source circuit to prevent current leakage.

DETAILED EXPLANATION OF THE PREFERRED EMBODIMENTS

Figure 1:
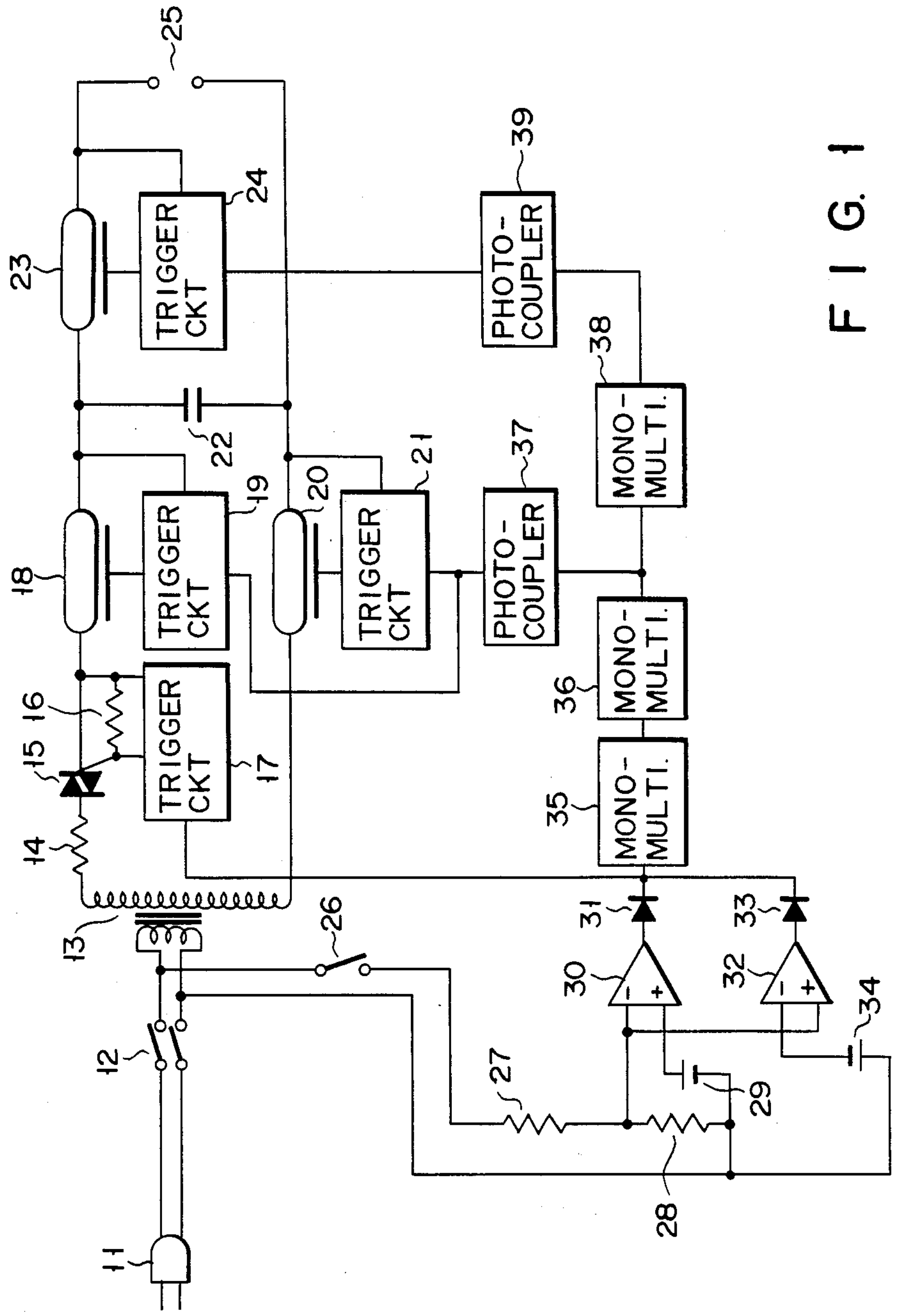
FIG. 1 is a circuit diagram of a stone disintegrator apparatus according to an embodiment of the present invention.

Referring to FIG. 1, power source plug 11 is connected to the primary winding of power source transformer 13 through power source switch 12. One end of the secondary winding of transformer 13 is connected to the input of triac 15 through resistor 14. The gate of triac 15 is connected to resistor 16 and trigger circuit 17. The output of triac 15 and the other end of transformer 13 are connected to discharge lamps 18 and 20, respectively. The trigger electrodes of lamps 18 and 20 are connected to trigger circuits 19 and 21, respectively. The outputs of lamps 18 and 20 are connected to both terminals of capacitor 22, respectively. One terminal of capacitor 22 is connected to one discharge electrode 25 through discharge lamp 23, and the other terminal of capacitor 22 is connected directly to the other discharge electrode 25. The trigger electrode of lamp 23 is connected to trigger circuit 24.

Power source switch 12 is connected to voltage-dividing resistors 27 and 28 through discharge switch 26. The node between resistors 27 and 28 is connected to the inverting input terminal of comparator 30 and the noninverting input terminal of comparator 32. Reference power sources 29 and 34 are respectively connected to the noninverting input terminal of comparator 30 and the inverting input terminal of comparator 32. The output terminals of comparators 30 and 32 are connected to trigger circuit 17 and monostable multivibrator 35 through diodes 31 and 33, respectively. The output terminal of multivibrator 35 is connected to photocoupler 37 and multivibrator 38 through multivibrator 36. The output terminal of photocoupler 37 is connected to trigger circuits 19 and 21. The output terminal of multivibrator 38 is connected to trigger circuit 24 through photocoupler 39.

Figure 2:
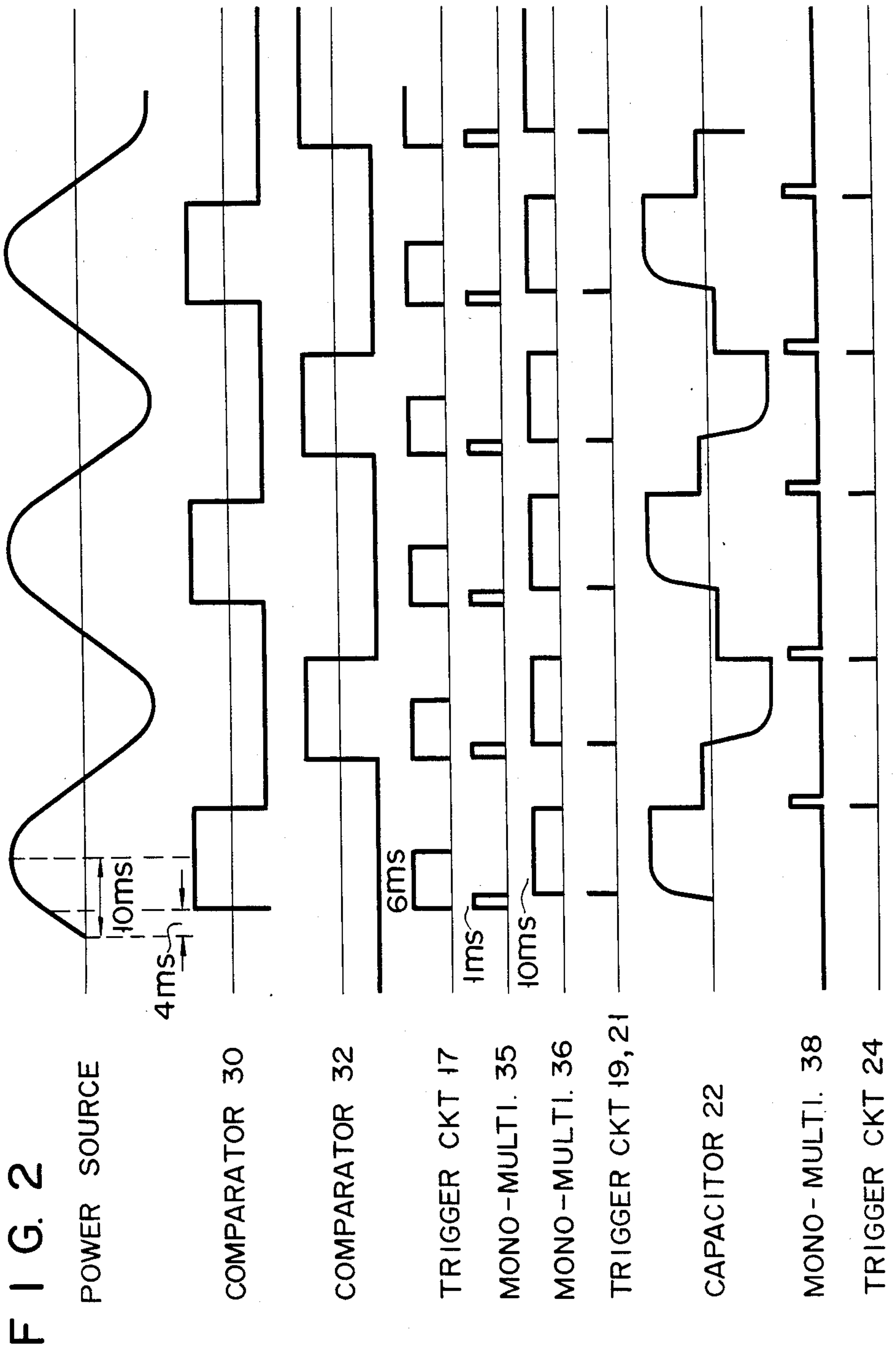
FIG. 2 is a timing chart for explaining the operation of the stone disintegrator apparatus of FIG. 1.

In the stone disintegrator apparatus of FIG. 1, when power source switch 12 is turned on, a voltage is induced at the secondary winding of power source transformer 13. When discharge switch 26 is turned on, a voltage obtained by dividing the power source voltage by the voltage-dividing resistors is applied to comparators 30 and 32. The output of comparator 30 is inverted to a positive value when the divided voltage exceeds the reference voltage from power source 29, as shown in the timing chart of FIG. 2. However, the output of comparator 32 is inverted to a positive value when the divided voltage is lower than the reference voltage from power source 29. It should be noted that the reference voltage is set to be a voltage appearing 4-msec after the zero-crossing point of the power source voltage. The output voltages of comparators 30 and 32 are applied to trigger circuit 17 and multivibrator 35 though diodes 31 and 33, respectively. Trigger circuit 17 and multivibrator 35 generate a 6-msec trigger pulse and a 1-msec pulse at the leading edges of output voltages of comparators 30 and 32. When trigger circuit 17 supplies a trigger pulse to the gate of triac 15, it is turned on. Thereafter, multivibrator 36 generates a 10-msec pulse in response to the trailing edge of the output pulse from multivibrator 35. The pulse from multivibrator 36 is supplied to trigger circuits 19 and 21 through photocoupler 37. Trigger circuits 19 and 21 generate trigger pulses in response to an output pulse from multivibrator 36 to trigger discharge lamps 18 and 20, respectively. When discharge lamps 18 and 20 are turned on, the power source voltage is applied to capacitor 22 to charge it. When capacitor 22 is charged up to the peak of the power source voltage, the power source voltage is lowered. A reverse voltage is applied to de-energize triac 15. Discharge lamps 18 and 20 are then turned off. In this state, capacitor 22 is completely charged. When ions in discharge lamps 18 and 20 disappear, the output pulse from multivibrator 36 falls. In response to the trailing edge of this pulse, multivibrator 38 generates an output pulse. This pulse is input to trigger circuit 24 through photocoupler 39, and trigger circuit 24 supplies a trigger pulse to discharge lamp 23. Discharge lamp 23 is turned on. Therefore, the charge voltage of capacitor 22 is applied to discharge electrode 25 through discharge lamp 23, and an electric discharge occurs at discharge electrode 25 so that a discharge arc disintegrates a stone. In this case, the discharge is an instantaneous discharge. When the instantaneous discharge is completed, the next power source cycle is started, i.e., the output of comparator 32 is inverted by the negative-cycle voltage. Pulses are generated by trigger circuit 17 and multivibrator 35 in response to the leading edge of the inverted pulse to turn on triac 15. After 1 msec, discharge lamps 18 and 20 are turned on in response to the output pulse from multivibrator 36. Capacitor 22 is then charged with a polarity opposite to the positive half cycle. At this moment, ions in discharge lamp 23 disappear. When discharge lamp 23 is turned on in response to the output pulse from multivibrator 38, a discharge occurs at discharge electrode 25 in a manner opposite the case of the positive half cycle, and the stone is disintegrated in the same manner as the discharge in the positive half cycle.

In the stone disintegrator apparatus as described above, the discharge circuit is completely isolated by discharge lamps 18 and 20 from the power source circuit, and at the same time trigger circuits 21, 19, and 24 are isolated by photocouplers 37 and 39. As a result, no current leakage occurs.

Figure 3:
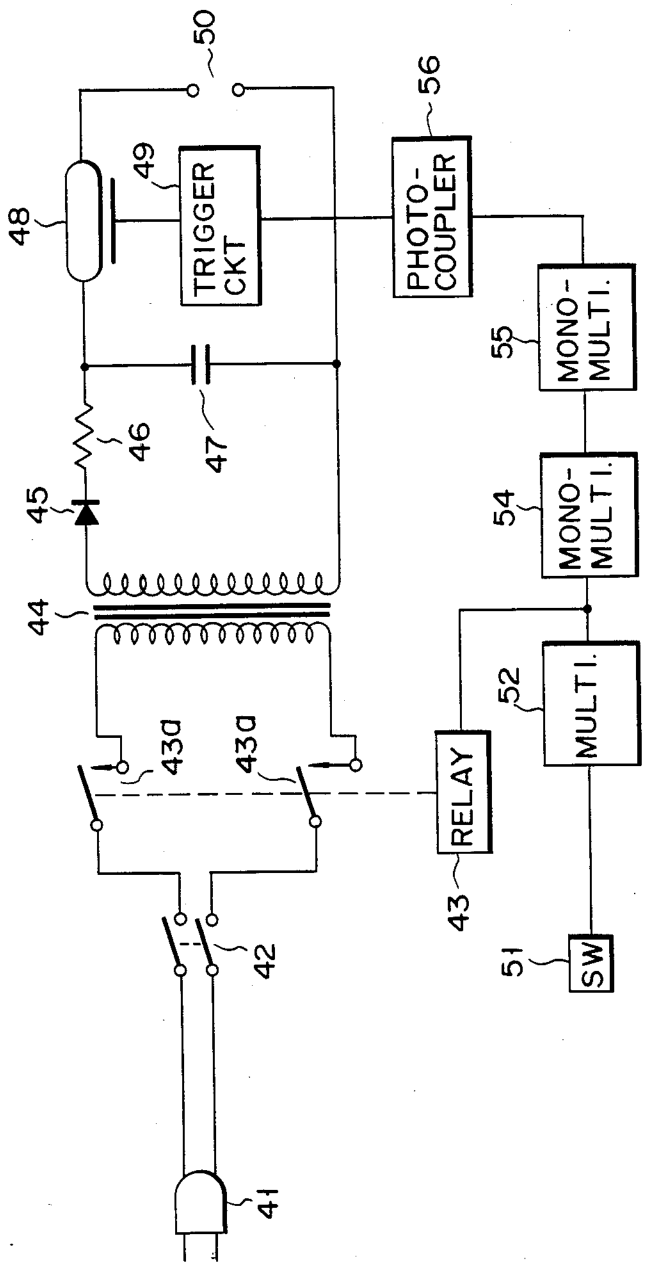
FIG. 3 is a circuit diagram of a stone disintegrator apparatus with a relay switch arranged at the primary winding of a transformer, according to another embodiment of the present invention.

According to another embodiment shown in FIG. 3, power source plug 41 is connected to power source transformer 44 through bipolar power source switch 42 and bipolar relay switch **43*a*. The secondary winding of transformer 44 is connected to capacitor 47 through diode 45 and resistor 46. Capacitor 47 is connected to discharge electrode 50 through discharge lamp 48**.

Discharge switch 51 is connected to relay 43 and monostable multivibrator 54 through multivibrator 52. The output terminal of multivibrator 54 is connected to trigger circuit 49 through monostable multivibrator 55 and photocoupler 56.

Figure 4:
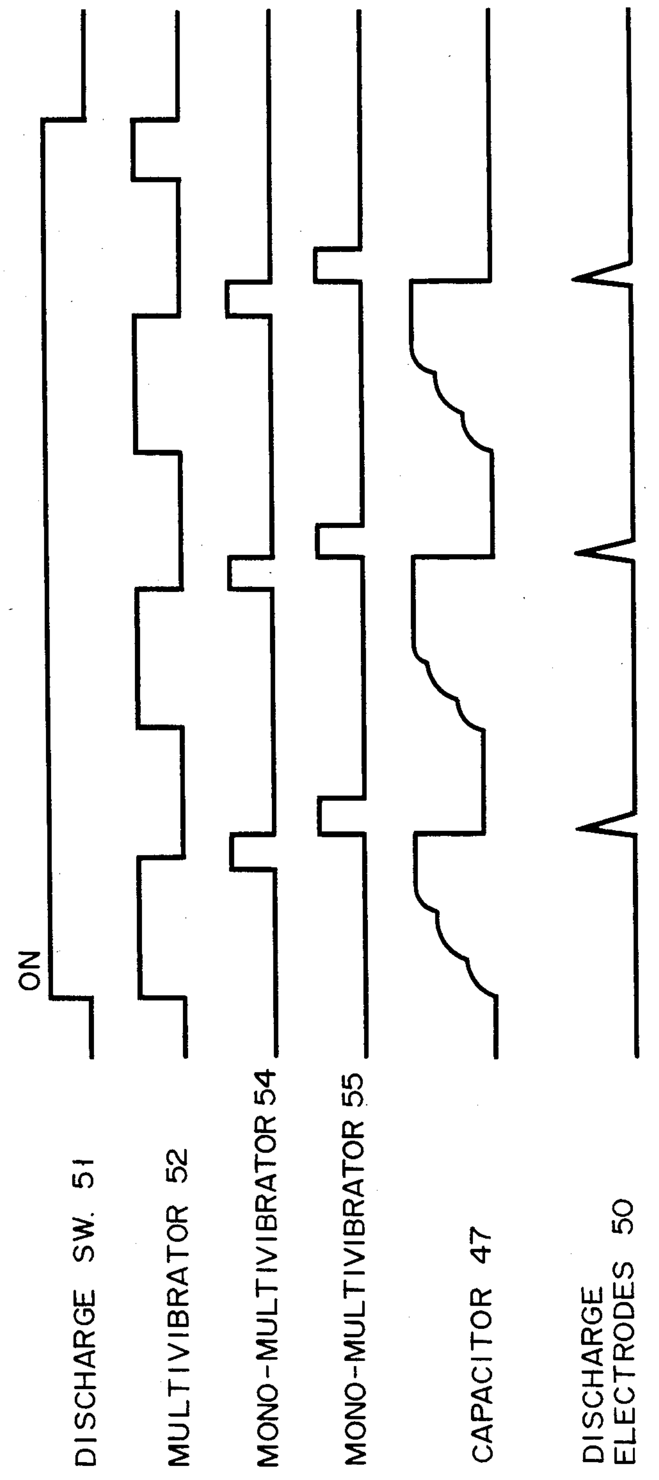
FIG. 4 is a timing chart for explaining the operation of the stone disintegrator apparatus in FIG. 3.

In a stone disintegrator apparatus of FIG. 3, when discharge switch 51 is turned on after power source switch 42 is turned on, as indicated in the timing chart of FIG. 4, the relay is energized in response to the output pulse from multivibrator 52 to close relay switch **43*a*. The secondary winding voltage of transformer 44 is rectified to charge capacitor 47. The output pulse from multivibrator 52 has a pulse width corresponding to three AC cycles, and capacitor 47 is charged by the 3-cycle rectification voltage up to a predetermined voltage. Upon completion of charging of capacitor 47, the output of multivibrator 52 falls to de-energize relay 43, thereby opening relay switch 43*a*. Multivibrator 54 generates a pulse in response to the trailing edge of the output from multivibrator 52. The pulse from multivibrator 54 has a pulse width for compensating the operation lag. Multivibrator 55 generates a pulse in response to the output from multivibrator 54. When the output pulse from multivibrator 55 is supplied to trigger circuit 49 through photocoupler 56, discharge lamp 48 is turned on and the charge voltage of capacitor 47 is applied to discharge electrode 50. A discharge arc is generated by electrode 50 to disintegrate the stone. Upon completion of this discharge, the charge and discharge cycle is repeated in response to the next pulse from multivibrator 52. This operation continues until discharge switch 51** is turned off.

In the embodiment of FIG. 3, the discharge circuit is completely isolated from the power source circuit during the discharge, and thus no current leakage occurs. During the charge, the capacitor is charged by the AC 3-cycle voltage. However, a voltage of one or other number of cycles may be used to charge the capacitor.

Figure 5:
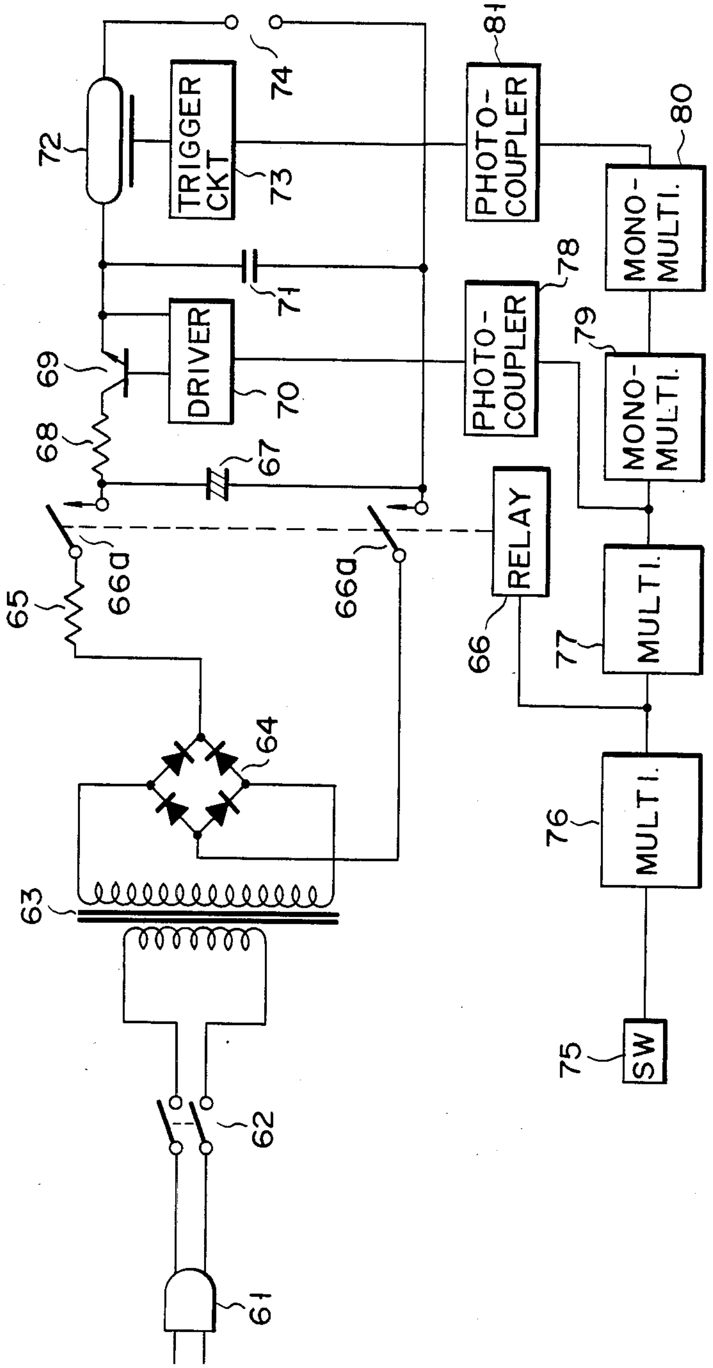
FIG. 5 is a circuit diagram of a stone disintegrator apparatus with a relay switch arranged at the secondary winding of a transformer, according to still another embodiment of the present invention.

In still another embodiment of FIG. 5, power source plug 61 is connected to power source transformer 63 through power source switch 62. Full-wave rectifier 64 is connected to the secondary winding of transformer 63. The output terminal of rectifier 64 is connected to capacitor 67 through relay 66 and bipolar relay switch **66*a*. Capacitor 67 is connected to capacitor 71 through resistor 68 and transistor 69. Driver 70 is connected to the base of transistor 69. Capacitor 71 is connected to discharge electrode 74 through discharge lamp 72. Lamp 72 is connected to trigger circuit 73**.

Discharge switch 75 is connected to relay 66 and multivibrator 77 through multivibrator 76. The output terminal of multivibrator 77 is connected to monostable multivibrator 79 and to driver 70 through photocoupler 78. The output terminal of multivibrator 79 is connected to trigger circuit 73 through monostable multivibrator 80 and photocoupler 81.

Figure 6:
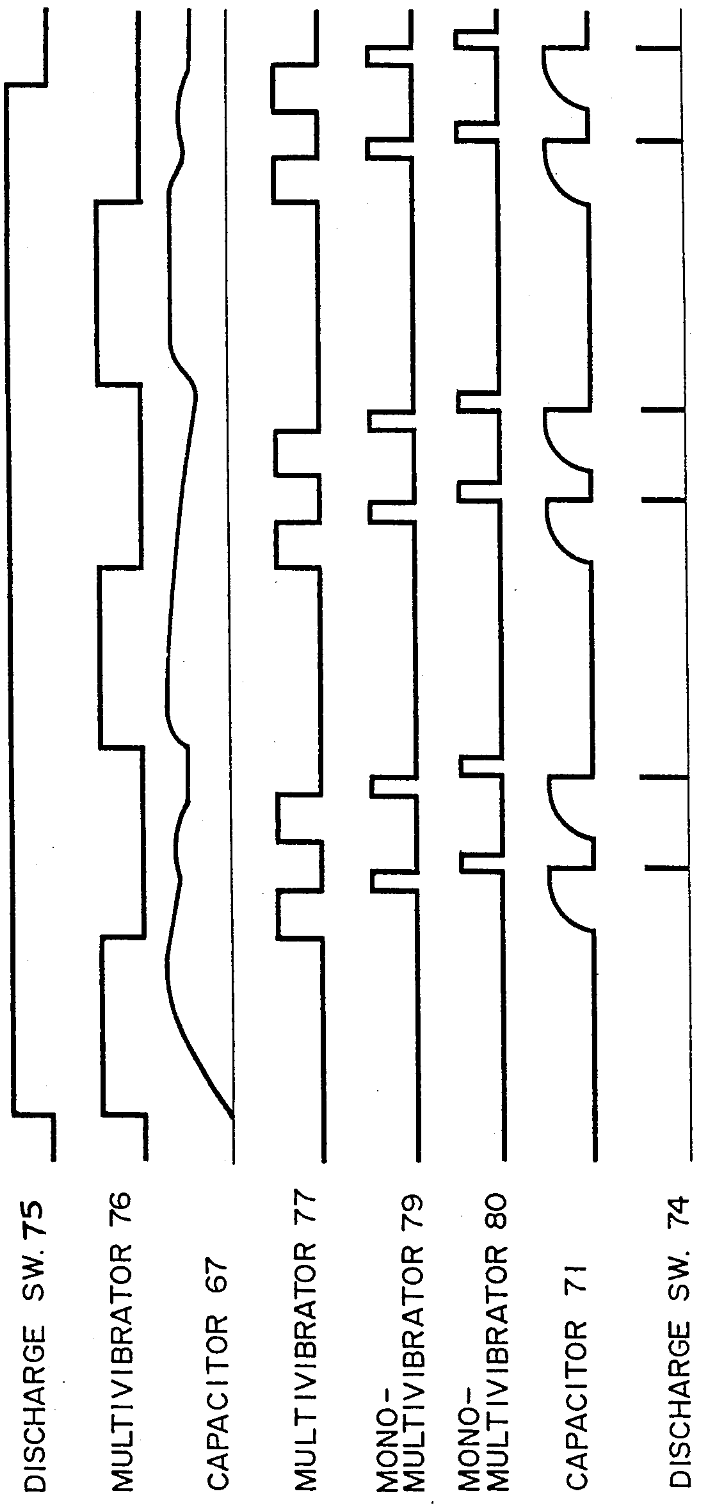
FIG. 6 is a timing chart for explaining the operation of the stone disintegrator apparatus in FIG. 5.

The operation of the stone disintegrator apparatus in FIG. 5 will be described with reference to the timing chart in FIG. 6. When discharge switch 75 is turned on after power source switch 62 is turned on, multivibrator 76 generates a pulse to energize relay 66. Relay switch **66*a* is then closed. At this time, a rectified output from full-wave rectifier 64 is supplied to charge capacitor 67 through resistor 65. Multivibrator 77 generates two pulses having a predetermined pulse width in response to the trailing edge of the output pulse from multivibrator 76. At the same time, relay 66 is deenergized to open relay switch 66*a*, and thus capacitor 67** is disconnected from the charge circuit.

The first pulse from multivibrator 77 is supplied to driver 70 through photocoupler 78 to turn on transistor 69 for a period corresponding to the pulse width. During this period, the charge of capacitor 67 is transferred to capacitor 71 through transistor 69. When the first pulse from multivibrator 77 falls, transistor 69 is turned off and multivibrator 79 generates a pulse. This pulse provides a delay time for stabilizing charging of capacitor 71.

Multivibrator 80 generates a pulse in response to the trailing edge of the pulse from multivibrator 79. The pulse from multivibrator 80 is supplied to trigger circuit 73 through photocoupler 81, and discharge lamp 72 is turned on. The charged voltage of capacitor 71 is supplied to discharge electrode 74, and a discharge occurs at discharge electrode 74 to disintegrate the stone.

The instantaneous discharge of discharge electrode 74 is completed, transistor 69 is turned on in response to the next pulse from multivibrator 77, and capacitor 71 is charged again by the charge of capacitor 67. Upon completion of charging of capacitor 67, an electric discharge occurs at electrode 74 to disintegrate the stone in the same operation as described above. When the arc discharge is completed, relay 66 is energized in response to the next pulse from multivibrator 76 to close relay switch 66a. Capacitor 67 is charged again, and the second arc discharge occurs in the same manner as described above.

According to the embodiment in FIG. 5, the discharge circuit is completely isolated from the power source circuit during the discharge. At the same time, one charge cycle of the capacitor by means of the power source circuit allows two arc discharge cycles, thus improving the stone disintegration rate. The number of arc discharge cycles is not limited to two, but may be arbitrarily set by changing the number of output pulses from multivibrator 77.

According to the above embodiment, since the discharge circuit is completely isolated from the power source circuit during the discharge, current leakage of the discharge capacitor does not occur. As a result, the dangerous state and wasteful power consumption caused by current leakage can be prevented.

Figure 7:
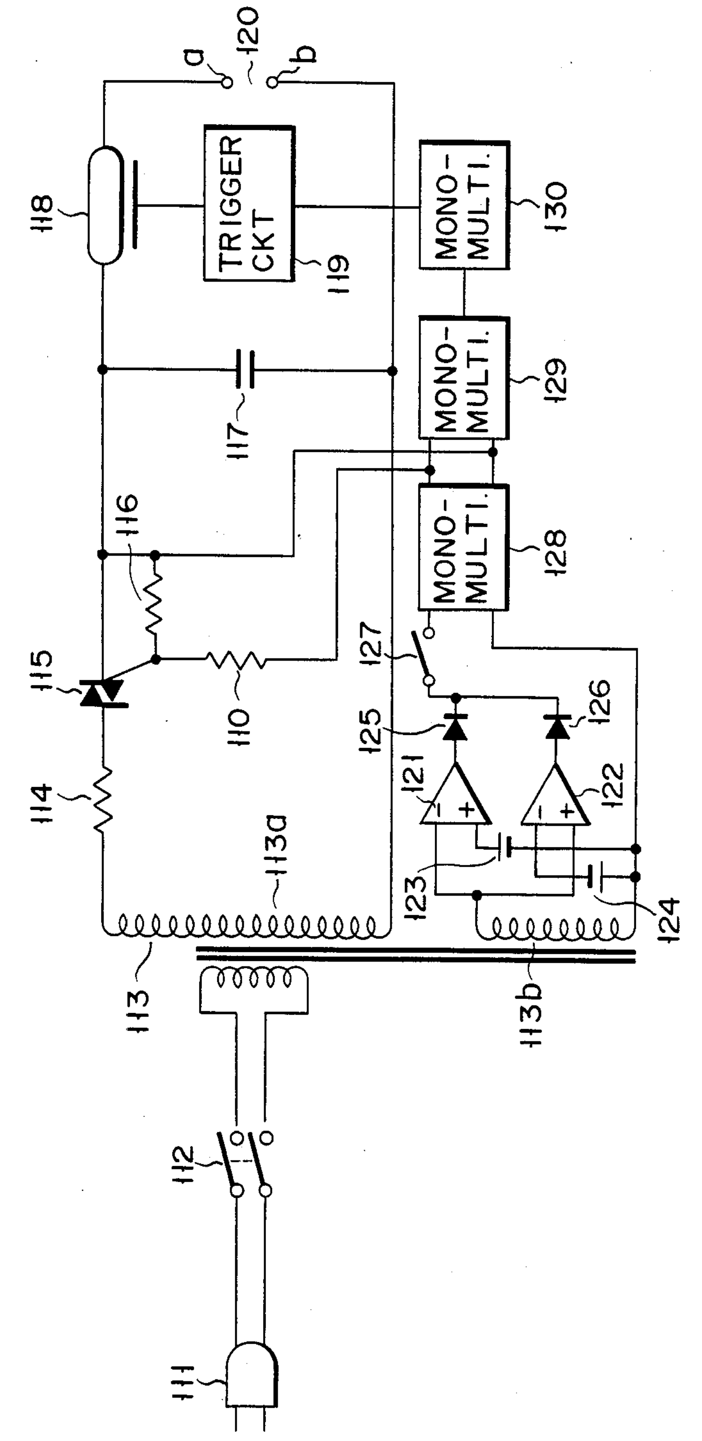
FIG. 7 is a circuit diagram of a stone disintegrator apparatus for switching between the charge and discharge modes in synchronism with an AC power source, according to still another embodiment of the present invention.

According to still another embodiment in FIG. 7, power source plug 111 is connected to the primary winding of power source transformer 113 through power source switch 112. One secondary winding 113a of transformer 113 is connected to capacitor 117 through resistor 114 and triac 115. The gate of triac 115 is connected to resistor 116. Capacitor 117 is connected to a probe electrode, i.e., discharge electrode 120 through discharge lamp 118. Trigger circuit 119 is connected to the trigger electrode of lamp 118.

Comparators 121 and 122 are connected to the other secondary winding 113b of transformer 113. The inverting input terminal of comparator 121 and the noninverting input terminal of comparator 122 are connected to secondary winding 113b. The noninverting input terminal of comparator 121 and the inverting input terminal of comparator 122 are connected to reference power sources 123 and 124, respectively. Therefore, if an AC output has a positive half cycle, comparator 121 outputs a positive output. However, comparator 122 generates a positive output if the AC output has a negative half cycle.

The output terminals of comparators 121 and 122 are connected to monostable multivibrator 128 through diodes 125 and 126 and discharge switch 127. The output terminal of multivibrator 128 is connected to monostable multivibrator 129 and to the gate of triac 115 through resistor 110. The output terminal of monostable multivibrator 129 is connected to trigger circuit 119 through monostable multivibrator 130.

Figure 8:
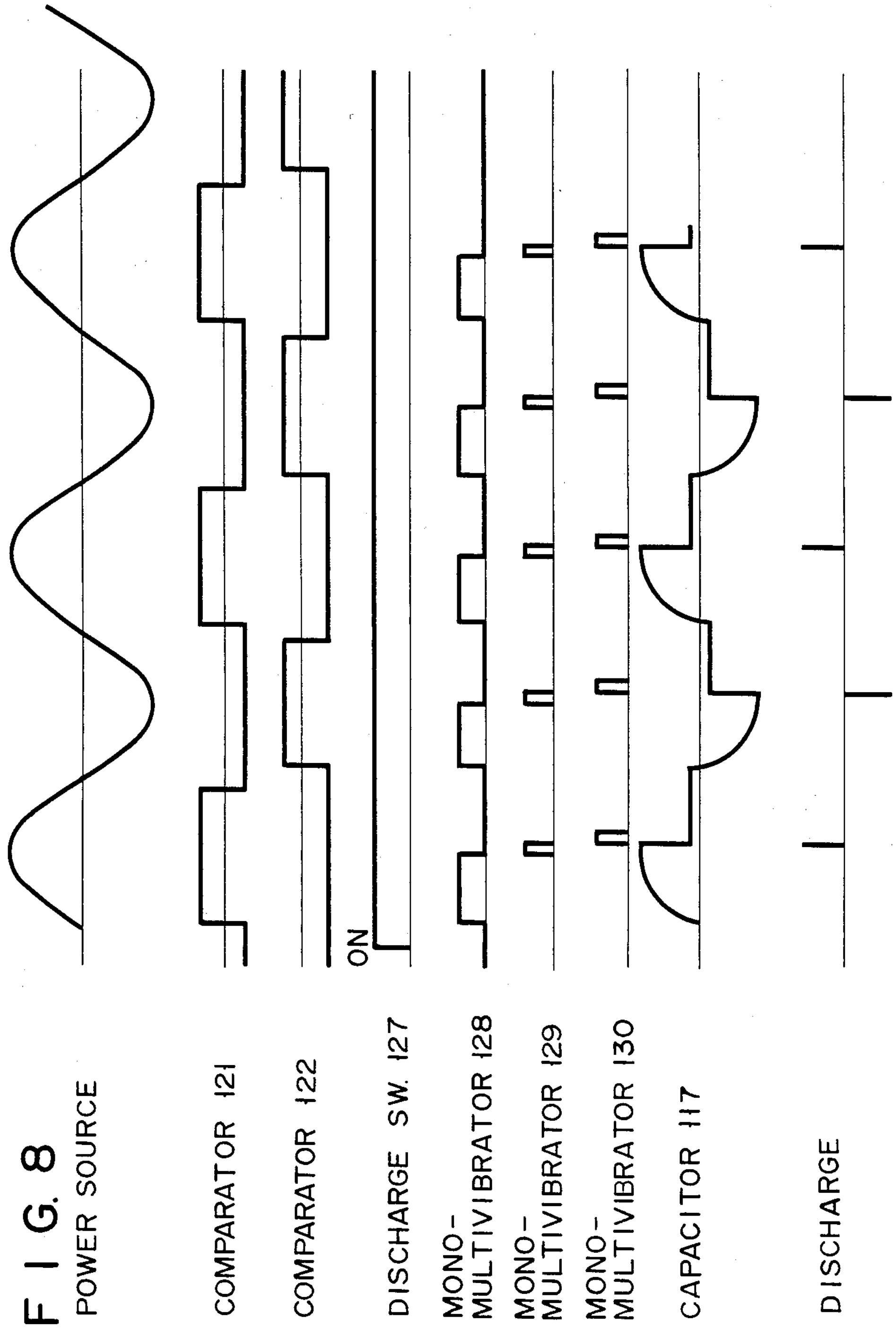
FIG. 8 is a timing chart for explaining the operation of the stone disintegrator apparatus in FIG. 7.

The operation of the stone disintegrator apparatus in FIG. 7 will be described with reference to the timing chart in FIG. 8. When power source switch 112 is turned on, AC voltage components appear at secondary windings 113a and 113b of power source transformer 113. When discharge switch 127 is then turned on, outputs from comparators 121 and 122 are supplied to monostable multivibrator 128 through diodes 125 and 126 and switch 127. In this case, during the positive half cycle of the AC voltage, comparator 121 generates a positive pulse if the AC voltage is higher than the reference voltage from reference power source 123. Comparator 122 generates a positive pulse if the AC voltage is lower than the reference voltage from reference power source 124.

When the output pulse from comparator 121 is supplied to monostable multivibrator 128, multivibrator 128 generates a pulse in response to the leading edge of comparator 121. A time constant of multivibrator 128 is set such that a 5-msec pulse is generated with respect to the power source frequency, e.g., 50 Hz for the following reason. Upon falling of the AC power source after triac 115 is energized in response to the output pulse from multivibrator 128, a reverse voltage is applied to triac 115 and is de-energized. It is thus useless to apply a gate pulse to triac 115. When triac 115 is energized, capacitor 117 is charged such that the discharge lamp 118 terminal of capacitor 117 is set at the positive polarity in the positive half cycle of the AC voltage. When capacitor 117 is charged to a maximum value of the AC voltage and the AC voltage starts to be lowered, triac 115 is turned off to complete charging of capacitor 117. At this time, monostable multivibrator 129 generates a 1-msec pulse in response to the trailing edge of the output from multivibrator 128. During the 1-msec period, the charging state of capacitor 117 is stabilized. Multivibrator 130 generates a pulse in response to the trailing edge of the output from multivibrator 129. When the pulse from multivibrator 130 is supplied to trigger circuit 119, discharge lamp 118 is turned on in response to a trigger pulse from trigger circuit 119. The voltage at capacitor 117 is applied to discharge electrode 120 through discharge lamp 118. In discharge electrode 120, an arc discharge occurs in a direction from electrode b to electrode a, and the arc disintegrates the stone.

Upon completion of the arc discharge, the output pulse from comparator 121 falls and then comparator 122 generates a pulse. Multivibrator 128 generates a 5-msec pulse in response to the leading edge of the pulse from comparator 122. Triac 115 is turned on in response to the 5-msec pulse. In this case, a voltage of the negative half cycle is applied to capacitor 117, and capacitor 117 is charged with a polarity opposite that in the case of the positive half cycle. In other words, the lamp 118 terminal of capacitor 117 is set at the negative polarity. When capacitor 117 is completely charged and lamp 118 is triggered in response to the trigger pulse from trigger circuit 119, capacitor 117 is discharged to discharge electrode 120 through lamp 118. In this case, since a voltage having a polarity opposite that in the case of the positive half cycle is applied to electrode 120, an arc discharge occurs in a direction from electrode a to electrode b.

As is apparent from the above description, the discharge direction is alternately changed in units of half cycles of the AC power source. One of electrodes a and b in discharge electrode 120 is not undesirably worn, and the service life of the electrode is substantially prolonged. In the above embodiment, the triac is used as the switching means. However, other semiconductor switches may be used in place of triacs.

Figure 9:
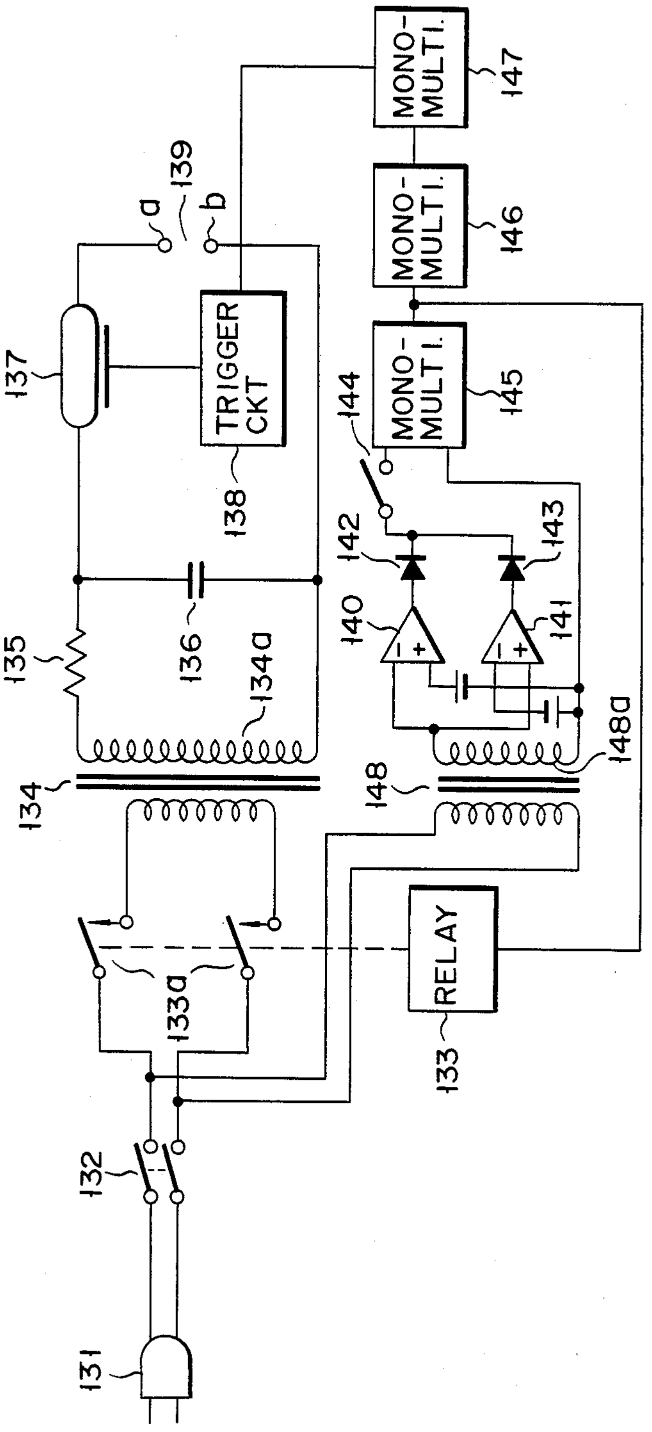
FIG. 9 is a circuit diagram of a stone disintegrator apparatus for switching between the charge and discharge modes in synchronism with an AC power source, according to still another embodiment of the present invention.

According to still another embodiment in FIG. 9, power source plug 131 is connected to the primary winding of power source transformer 134 through power source switch 132 and relay switch 133*a* of relay 133. One secondary winding 134*a* of transformer 134 is connected to capacitor 136 through resistor 135. Capacitor 136 is connected to discharge electrode 139 through discharge lamp 137. Trigger circuit 138 is connected to the trigger electrode of lamp 137.

Comparators 140 and 141 are connected to the secondary winding of transformer 148. The inverting input terminal of comparator 140 and the noninverting input terminal of comparator 141 are connected to secondary winding 148*a*. The noninverting input terminal of comparator 140 and the inverting input terminal of comparator 141 are connected to reference power sources, respectively. If the AC output has a positive half cycle, comparator 140 generates a positive output. However, if the AC output has a negative half cycle, comparator 141 generates a positive output.

The output terminals of comparators 140 and 141 are connected to monostable multivibrator 145 through diodes 142 and 143 and discharge switch 144. The output terminal of multivibrator 145 is connected to monostable multivibrator 146 and relay 133. The output terminal of multivibrator 146 is connected to trigger circuit 138 through multivibrator 147.

Figure 10:
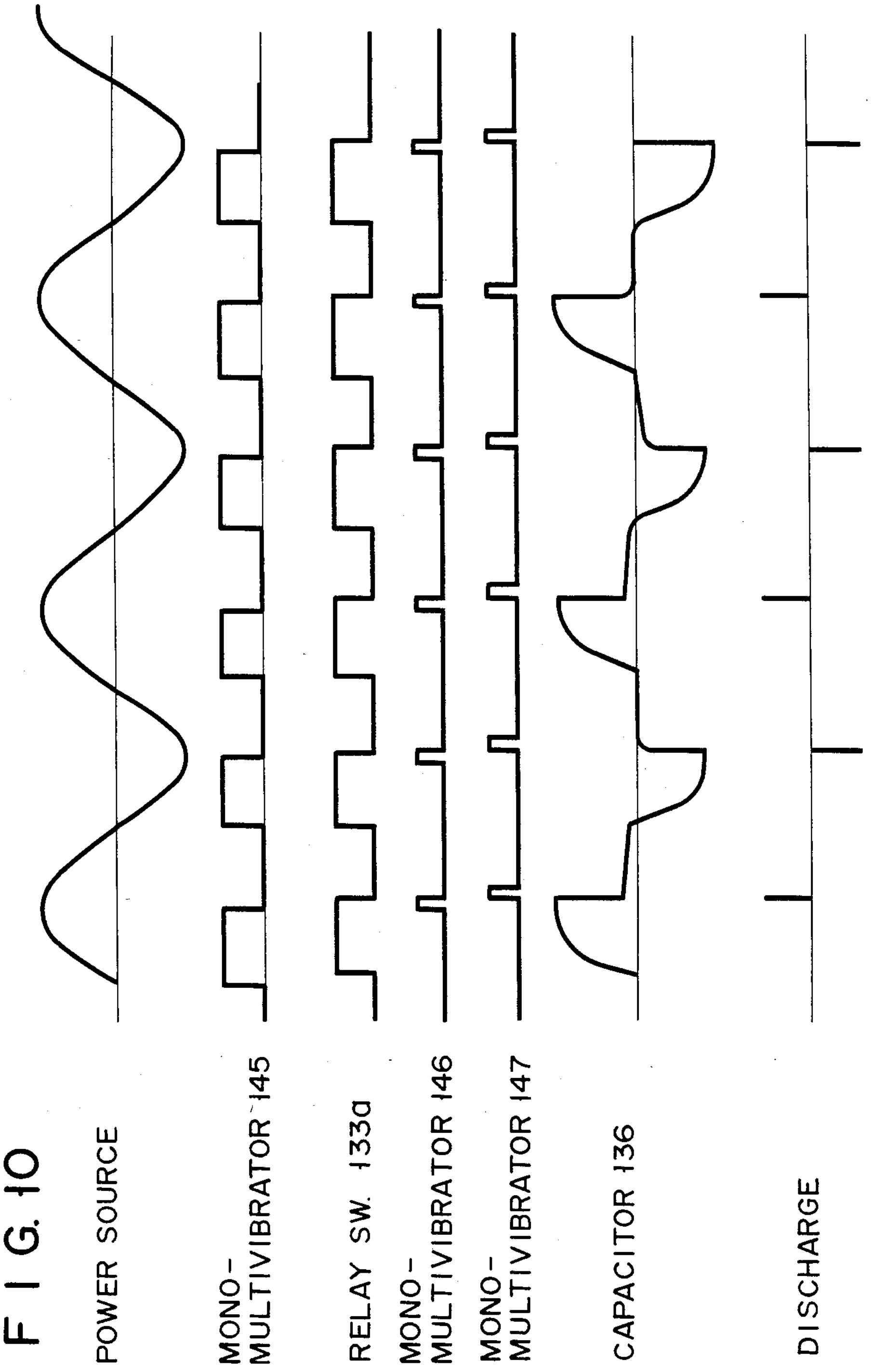
FIG. 10 is a timing chart for explaining the operation of the stone disintegrator apparatus in FIG. 9.

The operation of the stone disintegrator apparatus in FIG. 9 will be described with reference to the timing chart in FIG. 10. When discharge switch 144 is turned on after power source switch 132 is turned on, monostable multivibrator 145 generates a pulse. When this pulse is supplied to relay 133, relay 133 is energized to close relay switch 133*a* after a short delay time. An AC voltage is generated at the second winding of transformer 134, and capacitor 136 is charged such that its lamp 137 terminal is charged in the positive half cycle. Upon completion of charging of capacitor 136, the output pulse from multivibrator 145 falls to de-energize relay 133. Relay switch 133*a* is thus turned off after a short delay time, thereby stopping the charging of capacitor 136.

The pulse is generated by multivibrator 146 in response to the trailing edge of the output pulse generated from multivibrator 145 and has a pulse width for compensating the operation lag of relay 133. The pulse is supplied from multivibrator 147 to trigger circuit 138 in response to the trailing edge of the output pulse from multivibrator 146. In response to the pulse from multivibrator 147, trigger circuit 138 supplies a trigger pulse to the trigger electrode of discharge lamp 137 to turn it on. The voltage at capacitor 136 is applied to electrode 139 through lamp 137. An arc discharge occurs in a direction from electrode a to electrode b in discharge electrode 139. When the arc discharge is completed and then the next pulse is supplied from multivibrator 145 to relay 133, relay switch 133*a* is turned on, and capacitor 136 is charged with a polarity opposite that in the case of the negative half cycle of the AC power source. Upon completion of charging of capacitor 136, discharge lamp 137 is turned on and capacitor 136 is discharged. A voltage having a polarity opposite that in the case of the positive half cycle is applied to electrode 139 so that an arc discharge occurs in a direction from electrode b to electrode a.

According to the embodiment of FIG. 9, since capacitor 136 is discharged through resistor 135 and secondary winding 134*a* of transformer 134 while relay switch 133*a* is opened and until lamp 137 is triggered, the voltage level of capacitor 136 is slightly decreased. In this case, resistor 135 is connected to capacitor 136, so that no problem occurs in discharge. In addition, after the voltage of capacitor 136 has fallen to the discharge sustain voltage between discharge electrodes 139, the capacitor is discharged through secondary winding 134*a* until it is charged again. This facilitates the next charging of capacitor 136 as capacitor 136 is fully discharged.

In the above embodiment, each discharge is performed for every half cycle. However, after discharge cycles for one discharge direction are performed, discharge cycles for the other direction may be performed. The relay is used as the switching means but the switching means may be constituted by a semiconductor switch.

According to the above embodiment, a switching member is driven in synchronism with the cycle of the AC power source, and the capacitor is charged with one of the opposite polarities in units of half cycles in synchronism with the switching operation. Therefore, since voltages having opposite polarities are applied to the pair of electrodes constituting the discharge electrode, one of the electrodes is not undesirably worn, thus prolonging the service life of the discharge probe. Furthermore, since a special means is not required, cost is reduced and durability of the apparatus is improved.

What is claimed is:

1. A stone disintegrator apparatus comprising:
power source means;
a main capacitor to be charged by power from said power source means;
charging means for charging said main capacitor;
means for discharging said main capacitor;
electrode means coupled to said discharging means for generating an arc discharge on the basis of a charge on said main capacitor so as to disintegrate a stone in an internal organ;
said discharging means including first switching means connected between said main capacitor and the electrode means for, when turned on, selectively leading charges discharged from said main capacitor to said electrode means;
said charging means including means for isolating said power source means electrically from said discharge means by being off at least during discharge of the main capacitor; and
delay means for turning on said first switching means to pass current therethrough only after lapse of a predetermined time period from when said isolating means turns off to block current therethrough.

2. An apparatus according to claim 1, wherein said isolating means comprises at least one discharge lamp connected between said power source means and said main capacitor, and means for turning on said at least one discharge lamp during only charging of said main capacitor.

3. An apparatus according to claim 2, wherein said power source means comprises first and second output terminals, and said isolating means comprises two discharge lamps respectively coupled to said first and second output terminals.

4. An apparatus according to claim 1, wherein said power source means comprises alternating current power source means for generating an alternating current output, and said charging means further comprises second switching means connected between said power source means and said main capacitor through said isolating means, and means for energizing said second switching means in units of half cycles of the alternating current output.

5. An apparatus according to claim 4, wherein said power source means comprises first and second output terminals, and said isolating means comprises two discharge lamps respectively connected to said first and second output terminals through said second switching means.

6. An apparatus according to claim 4, wherein said charging means further comprises means for energizing said second switching means for a predetermined period of time in units of half cycles of the alternating current output.

7. An apparatus according to claim 6, wherein said isolating means comprises at least one discharge lamp.

8. An apparatus according to claim 1, wherein said isolating means comprises relay means for isolating said main capacitor from said power source means.

9. An apparatus according to claim 8, wherein said isolating means further comprises means for generating a pulse having a predetermined width, and said relay means comprises relay switching means for disconnecting said power source means in response to the pulse.

10. An apparatus according to claim 9, wherein said power source means comprises a power source transformer having primary and secondary windings, and said relay switching means is connected to said primary winding of said power source transformer.

11. An apparatus according to claim 9, wherein said power source means comprises a power source transformer having primary and secondary windings, and rectifying means connected to said secondary winding, said rectifying means being provided with output means for outputting a direct current component, and said relay switching means is connected between said charging means and output means of said rectifying means.

12. An apparatus according to claim 11, wherein said charging means comprises an auxiliary capacitor connected to said rectifying means through said relay switching means and charged in response to the direct current component from said rectifying means, and switching means, connected between said auxiliary and main capacitors, for supplying a charge output of said auxiliary capacitor to said main capacitor for every discharge for disintegrating the stone.

13. An apparatus according to claim 12, wherein said switching means comprises means for supplying power to said main capacitor at least twice with respect to one charging cycle of said auxiliary capacitor.

14. An apparatus according to claim 1, wherein said power source means comprises alternating current power source means for generating an alternating current output, and said isolating means comprises switching means operated in synchronism with the alternating current output from said alternating current power source.

15. An apparatus according to claim 14, wherein said switching means comprises a triac connected to an output of said alternating current power source.

* * * * *